(12) United States Patent
Tashiro et al.

(10) Patent No.: US 7,135,041 B2
(45) Date of Patent: Nov. 14, 2006

(54) ARTIFICIAL VISION SYSTEM

(75) Inventors: Hiroyuki Tashiro, Aichi (JP); Yasuo Terasawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 341 days.

(21) Appl. No.: 10/650,846

(22) Filed: Aug. 29, 2003

(65) Prior Publication Data

US 2004/0054407 A1    Mar. 18, 2004

(30) Foreign Application Priority Data

Aug. 30, 2002  (JP) ............................. P2002-253944

(51) Int. Cl.
*A61F 2/16* (2006.01)
(52) U.S. Cl. .................. 623/6.22; 623/6.43; 623/6.63; 607/53; 607/54
(58) Field of Classification Search ................. 607/54, 607/53; 623/6.22, 6.35, 6.43, 6.63
See application file for complete search history.

(56) References Cited

U.S. PATENT DOCUMENTS

| | | | | |
|---|---|---|---|---|
| 4,601,545 A | * | 7/1986 | Kern ........................... 349/200 |
| 4,628,933 A | * | 12/1986 | Michelson .................... 607/53 |
| 4,787,903 A | * | 11/1988 | Grendahl ..................... 623/6.22 |
| 5,106,179 A | | 4/1992 | Kamaya et al. |
| 5,147,284 A | * | 9/1992 | Fedorov et al. ................. 600/9 |
| 5,935,155 A | * | 8/1999 | Humayun et al. ............. 607/54 |
| 6,120,538 A | * | 9/2000 | Rizzo et al. ................ 623/6.11 |
| 6,427,087 B1 | * | 7/2002 | Chow et al. .................. 607/54 |
| 6,847,847 B1 | * | 1/2005 | Nisch et al. .................. 607/54 |
| 6,976,998 B1 | * | 12/2005 | Rizzo et al. ................ 623/6.63 |
| 2004/0078064 A1 | * | 4/2004 | Suzuki ......................... 607/54 |

FOREIGN PATENT DOCUMENTS

| WO | 94/26209 A1 | 11/1994 |
|---|---|---|
| WO | 96/39221 A1 | 12/1996 |
| WO | 99/45870 A1 | 9/1999 |
| WO | 02/064072 A1 | 8/2002 |
| WO | 08/080828 A1 | 10/2002 |

* cited by examiner

*Primary Examiner*—David H. Willse
*Assistant Examiner*—Javier G. Blanco
(74) *Attorney, Agent, or Firm*—Sughrue Mion, PLLC

(57) ABSTRACT

An artificial vision system for regenerating or restoring vision of an eye of a patient includes: a power acquiring unit which is disposed inside the eye, includes a magnetic core having an opening and a coil wound around the magnetic core, and is adapted to acquire power from outside a body using electromagnetic induction; and a plurality of electrodes which is provided at a retina and is adapted to electrically stimulate cells constituting the retina.

12 Claims, 6 Drawing Sheets

ARTIFICIAL VISION SYSTEM

BACKGROUND OF THE INVENTION

The present invention relates to an artificial vision system for regenerating or restoring vision.

Recently, a study has been conducted on an artificial vision system that promotes regeneration or restoration of vision by electrically stimulating cells forming the retina with electrodes or the like placed inside the eye. As such an artificial vision system, there are a type that stimulates cells based on an image picked up outside the body (hereinafter, referred to as the external imaging type), a type that stimulates cells based on an image formed on photodiode arrays or the like placed inside the eye (hereinafter, referred to as the internal imaging type), etc.

Regarding the artificial vision system described as above, in order to supply an apparatus to be placed inside the eye with power wirelessly from outside the body, there has been discussed a method of supplying power through electromagnetic induction using a primary coil placed outside the body and a secondary coil placed inside the eye.

However, when a frequency band and magnitude of electromagnetic waves suitable for use in a human body are concerned, it is difficult to supply required power with the secondary coil having an air core, that is, having no magnetic core, and therefore a coil having a magnetic core has to be used. Nevertheless, a coil having a magnetic core is so heavy that it is not suitably placed inside the eye. Moreover, when a coil having a magnetic core is placed in the vicinity of the anterior ocular segment, incoming light from outside the eye may possibly be blocked by the magnetic core in the case of the artificial vision system of the internal imaging type.

SUMMARY OF THE INVENTION

The invention was devised in view of the foregoing, and a technical challenge to be met by the invention is therefore to provide an artificial vision system that can efficiently supply an apparatus to be placed inside the eye with power while being used suitably.

In order to solve the aforesaid object, the invention is characterized by having the following arrangement.

Aspect 1. An artificial vision system for regenerating or restoring vision of an eye of a patient comprising:
  a power acquiring unit which is disposed inside the eye, includes a magnetic core having an opening and a coil wound around the magnetic core, and is adapted to acquire power from outside a body using electromagnetic induction; and
  a plurality of electrodes which is provided at a retina and is adapted to electrically stimulate cells constituting the retina.

Aspect 2. The artificial vision system according to the aspect 1, wherein the power acquiring unit is disposed so that the opening of the magnetic core is located at a pupil.

Aspect 3. The artificial vision system according to the aspect 2, wherein the opening of the magnetic core is made as large as or larger than a maximum size of the pupil.

Aspect 4. The artificial vision system according to the aspect 2 further comprising a plurality of light-receiving elements which are provided so as to correspond to the plurality of electrodes and disposed inside the eye so as to receive light from outside the body through the opening of the magnetic core.

Aspect 5. The artificial vision system according to the aspect 4 further comprising an optical member which is disposed on an axis of the magnetic core and is adapted to form an image of an object point at a predetermined distance position in front of the eye on a light-receiving surface of the plurality of light-receiving elements.

Aspect 6. The artificial vision system according to the aspect 5, wherein the optical member is placed in the opening of the magnetic core.

Aspect 7. The artificial vision system according to the aspect 5 further comprising a moving unit which is adapted to moves the optical member in an axial direction of the magnetic core.

Aspect 8. The artificial vision system according to the aspect 2, wherein an iris pattern is provided to one of the magnetic core, a substrate on which the magnetic core is disposed and a coating surface embedding the magnetic core.

Aspect 9. The artificial vision system according to the aspect 2 further comprising a power supply unit which is disposed in front of the eye, includes a magnetic core having an opening and a coil wound around the magnetic core, and is adapted to supply the power to the power acquiring unit using the electromagnetic induction.

The present disclosure relates to the subject matter contained in Japanese patent application No. 2002-253944 (filed on Aug. 30, 2003), which is expressly incorporated herein by reference in their entireties.

DETAILED DESCRIPTION OF PREFERRED EMBODIMENTS

Figure 1:
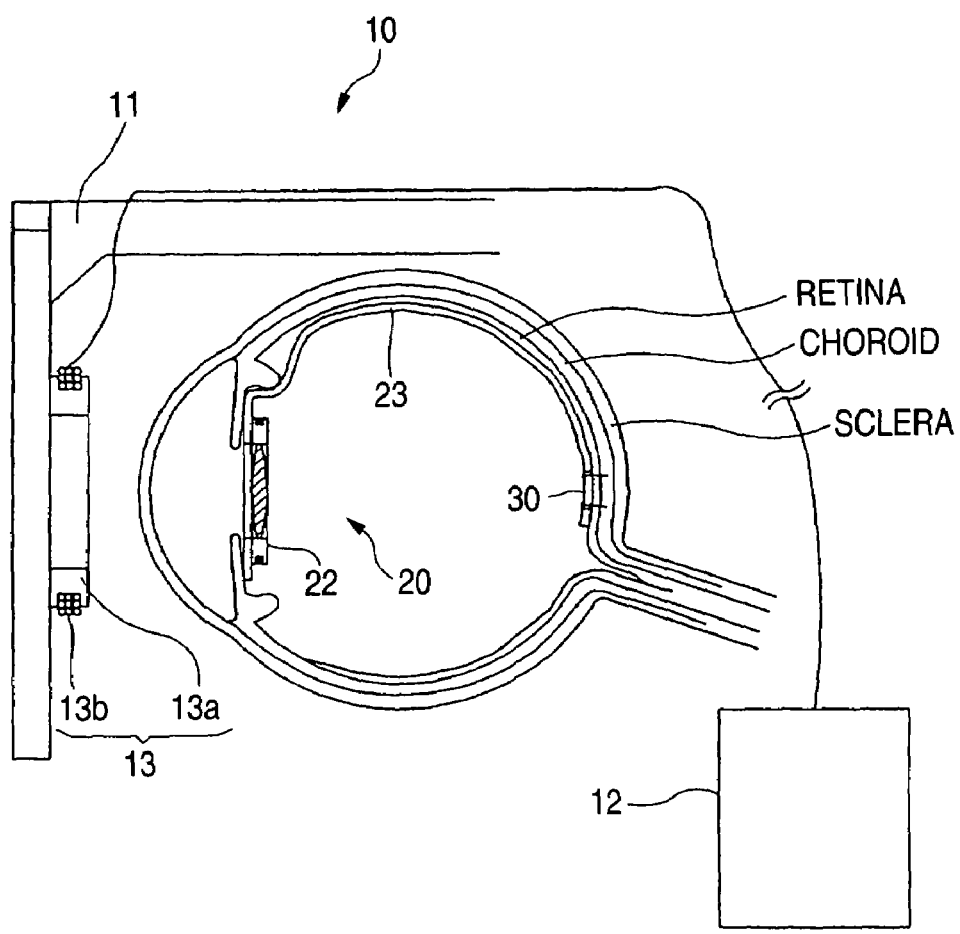
FIG. 1 is a schematic diagram of an artificial vision system of an internal imaging type in one embodiment of the invention.

The following description will describe one embodiment of the invention with reference to the drawings. FIG. 1 is a schematic diagram of an artificial vision system of the internal imaging type in the embodiment.

The artificial vision system is roughly divided into an external apparatus 10 placed outside the body and an internal apparatus 20 placed inside the eye. The external apparatus 10 includes a visor 11 that the user (blind person) can use as if he put eyeglasses on, and a power apparatus 12. The visor 11 is provided with a power supply portion 13 used to supply the internal apparatus 20 with power from the power apparatus 12. The power supply portion 13 includes a hollow (ring-shaped) magnetic core 13a, and a primary coil 13b wound around the magnetic core 13a. The magnetic core 13a may be made of a material generally used for a magnetic body, such as ferrite. The primary coil 13b may be made of a material that can be generally used for coil wires, such as copper, gold, and platinum.

It is arranged in such a manner that the power supply portion 13 is situated in front of the eye of the user when the user puts on the visor 11. Because the power supply portion 13 has the hollow magnetic core 13a (has an opening), the user's view is not blocked even when the power supply portion 13 is situated in front of the eye.

Meanwhile, the internal apparatus 20 includes a power acquiring portion 22 and a vision regenerating portion 30 both attached onto a substrate 23. The vision regenerating portion 30 is electrically connected to the power acquiring portion 22 through an electrical line 21 (see FIG. 2).

Figure 2:
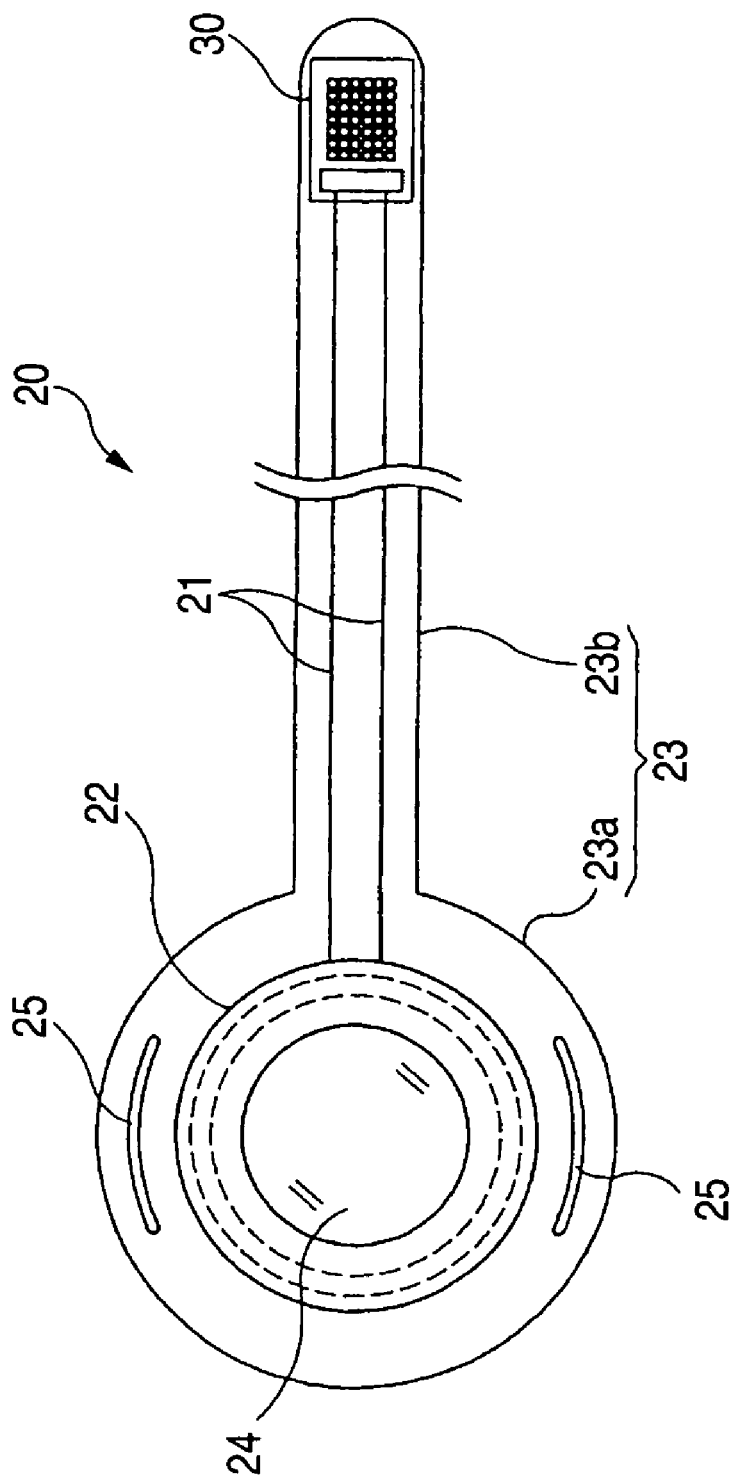
FIG. 2 is a schematic diagram of an internal apparatus.

FIG. 2 is a schematic diagram of the internal apparatus 20. A material having good biocompatibility as well as a light transmitting property is used for the substrate 23, and polyimide is used in the embodiment. The substrate 23 comprises a disc portion 23a and a long-plate portion 23b. The power acquiring portion 22 is attached to the disc portion 23a, and the vision regenerating portion 30 is attached to the tip end of the long-plate portion 23b. The long-plate portion 23b in the embodiment has such a length that the vision regenerating portion 30 located at the tip end is situated in the vicinity of the macula of retina along the retina when the disc portion 23a is placed behind the iris in the vicinity thereof. Hence, a length of the substrate 23 from a position at which the power acquiring portion 22 is placed to a position at which the vision regenerating portion 30 is placed is preferably about 20 mm to 40 mm, and more preferably about 25 mm to 35 mm.

Figure 3A:
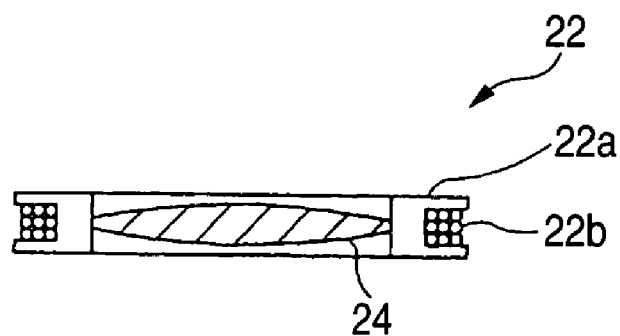
FIGS. 3A and 3B are schematic diagrams of a power acquiring portion.

As shown in the cross section of FIG. 3A, the power acquiring portion 22 includes a hollow (ring-shaped) magnetic core 22a, and a secondary coil 22b wound around the magnetic core 22a. The magnetic core 22a may be made of a material generally used for a magnetic body, such as ferrite. The secondary coil 22b may be made of a material that can be generally used for coil wires, such as copper, gold, and platinum.

In the embodiment, light from outside the eye is introduced to the eye (fundus) ground through an opening in the magnetic core 22a by situating the opening in the magnetic core 22a at the pupil. For this reason, it is preferable that the opening of the magnetic core 22a is made as large as or larger than the maximum size of the pupil. For example, it is sufficient to provide an opening of about 2 mm to 7 mm.

An optical member (lens) 24 to serve as the crystalline lens of eye is placed in the opening in the magnetic core 22a of the embodiment, which makes it possible to form an image of a given object point at a predetermined distance position in front of the user's eyes on a light-receiving surface of the vision regenerating portion 30 that will be described below. It should be appreciated that the optical member 24 can be placed anywhere on the axis of the magnetic core 22a. For example, it may be placed in front or behind the magnetic core 22a. On the other hand, in a case where the crystalline lens of eye is not removed when the internal apparatus 20 is placed inside the eye, the optical member 24 may be omitted.

Figure 3B:
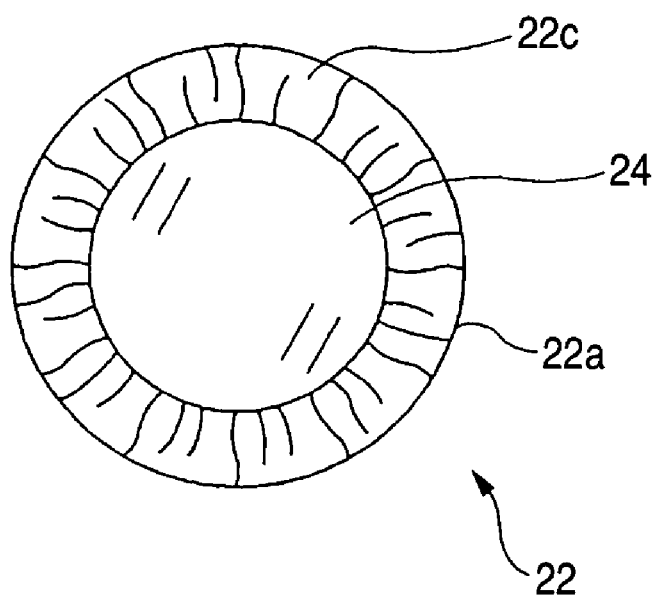

Also, as shown in the plan view of FIG. 3B, an iris pattern 22c is provided to one surface of the magnetic core 22a (the surface situated on the iris side when placed inside the eye, the surface that comes in contact with the substrate 23 in the embodiment). The iris pattern 22c may be provided to a portion to be placed on the periphery of the iris, for example, on the disc portion 23a of the substrate 23 or a coating surface that embeds the magnetic core 22a.

Figure 4A:
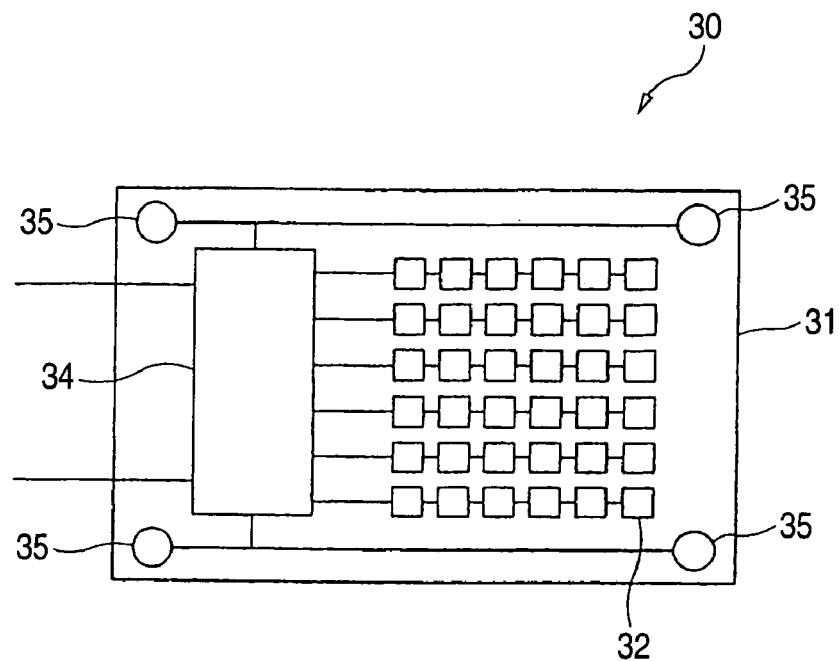
FIGS. 4A and 4B are schematic diagrams of a vision regenerating portion.
Figure 4B:
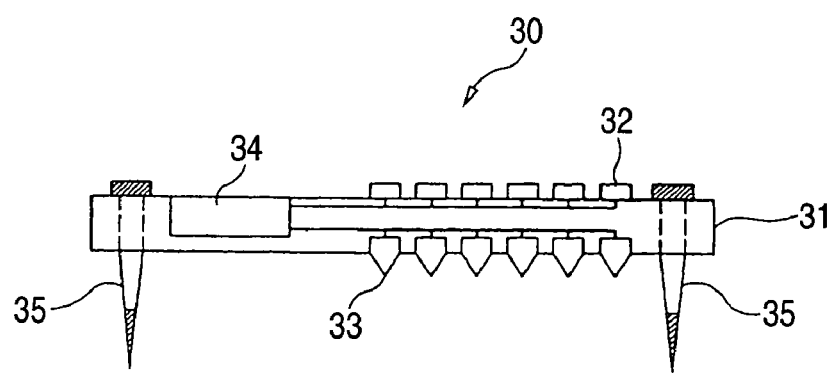

As shown in the plan view of FIG. 4A and the cross section of FIG. 4B, the vision regenerating portion 30 includes a base 31 provided on the substrate 23, light-receiving elements 32 comprising photodiodes or the like stimulating electrodes 33, a control circuit 34, etc., which are provided to the base 31, and thereby has an IC (Integrated Circuit) structure.

As shown in FIG. 2, a number of light-receiving elements 32 are provided in two-dimensional arrays to the base 31 on the surface on the same side where the power acquiring portion 22 is provided on the substrate 23 (on the paper surface side of FIG. 2). Further, the stimulating electrodes 33 in the matching number with the light-receiving elements 32 are correspondingly provided in two-dimensional arrays to the base 31 on the surface opposite to the surface on which the light-receiving element 32 are provided (on the overleaf side of FIG. 2). The stimulating electrodes 33 penetrate through the substrate 23 and are exposed to the outside, so that each stimulating electrode 33 is allowed to come in direct contact with the retina at the tip end when the internal apparatus 20 is placed inside the eye. The respective light-receiving elements 32 and the respective Stimulating electrodes 33 are connected to the control circuit 34 individually through electrical lines (FIGS. 4A and 4B show a state where a plurality of light-receiving elements 32 and stimulating electrodes 33 are connected to the control circuit 34 in groups for ease of explanation).

Numeral 35 denotes tacks used to fixedly hold the vision regenerating portion 30 on the retina. Each tack 35 is shaped like a needle, and four tacks 35 are attached integrally to the base 31 so as to extend respectively from four corners of the base 31 by a certain length in a direction along which the stimulating electrodes 33 protrude. In order to fixedly hold the vision regenerating portion 30, the tacks 35 have a length such that the tip ends thereof reach the choroid or the sclera when they are pushed into the retina to be fully inserted. By inserting the tacks 35 to pierce through the retina and reach the choroid or the sclera, the retina is positioned between the tip ends of the tacks 35 and the stimulating electrodes 33.

The tacks 35 are made of a material having electrical conductivity, such as titanium and platinum; moreover, the tacks 35 are insulated with coating except for the tip ends and the rear ends (shaded portions of FIG. 4B). The rear end portions (non-insulated portions) of the tacks 35 have been electrically connected to the control circuit 34. The tacks 35 and the stimulating electrodes 33 are thereby electrically connected to each other, and the tacks 35 serve as reference electrodes.

The tacks 35 have been provided fixedly (integrally) to the base 31 in the embodiment. It should be appreciated, however, that the invention is not limited to this arrangement, and the base 31 may have been provided with only through-holes for the tacks 35 to penetrate through in advance. In such a case, for example, the base 31 is coated with an electrically conducting material in portions that come in contact with the rear ends of the tacks 35 when the tacks 35 are fit into the through-holes provided in the base 31, and the coated portions are thereby electrically connected to the control circuit 34. On the other hand, the tacks 35 are insulated except for the tip ends and the rear ends, and when the base 31 is fixed onto the retina with the use of the tacks 35, the rear ends of the tacks 35 come in contact with predetermined portions of the through-holes coated with the electrical conducting material.

Numeral 25 denotes openings provided in the disc portion 23a. The openings 25 are formed to situate at positions where no influence of dynamic interference of the iris is given when the disc portion 23a is placed behind the iris. The openings 25 are used to suture the disc portion 23a and the iris together to be fixed inside the eye when the internal apparatus 20 is placed inside the eye.

After the power acquiring portion 22, the vision regenerating portion 30, etc. are attached to the substrate 23, the internal apparatus 20 is coated entirely with a material having good biocompatibility, such as polyimide, so that body fluid or the like will not come in contact with machines forming the internal apparatus 20. In this instance, neither the electrodes 33 nor the tip ends of the tacks 35 are coated, so that they are allowed to come in direct contact with a living body.

Figure 5:
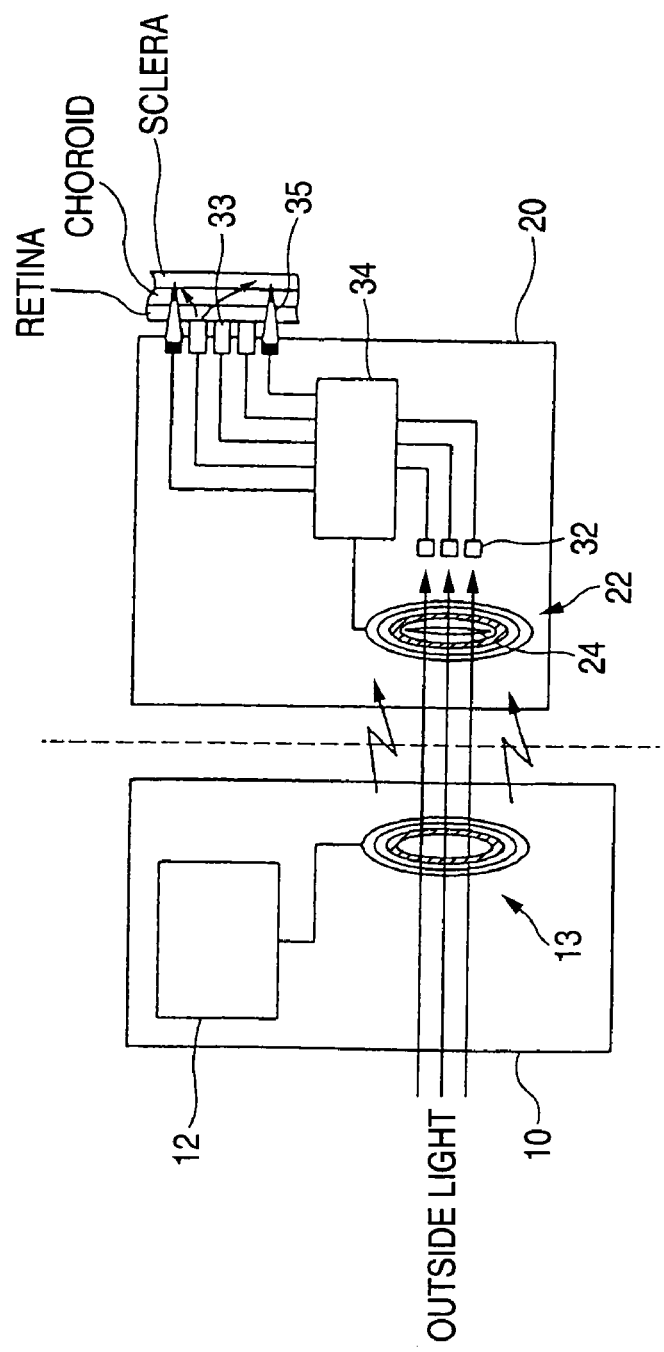
FIG. 5 is a schematic block diagram showing a control system in the artificial vision system in the embodiment.

Operations of the artificial vision system arranged as above will be described with reference to the block diagram of a control system of FIG. 5.

Initially, the crystalline lens in the patient's eye (user's eye) is removed through phacoemulsification and aspiration using a known apparatus for cataract surgery or the like. Then, an insertion opening is made by incising the sclera by a predetermined quantity or so in a region at a predetermined distance (for example, about 1.5 mm) from the peripheral cornea on the ear side, and the internal apparatus 20 is inserted into the eye through the insertion opening. The long-plate portion 23b is placed along the retina, so that the vision regenerating portion 30 is situated on the retina in the vicinity of the macula of retina. The vision regenerating portion 30 is fixed inside the eye by pushing the tacks 35 into the retina. When the tacks 35 are pushed into the retina, the tacks 35 penetrate through the retina and the tip ends reach the choroid or the sclera, whereby the vision regenerating portion 30 is fixedly held on the retina.

On the other hand, the disc portion 23a is placed behind the iris in the anterior ocular segment, and the opening in the magnetic core 22a is situated at the pupil. Subsequently, a suture thread is put through the openings 25 provided in the disc portion 23a to suture the iris and the disc portion 23a together. The disc portion 23a is thus fixedly held in the anterior ocular segment. Alternatively, instead of the iris, the openings 25 and the periphery of the ciliary body may be sutured together. In this case, the disc portion 23a needs to have a diameter large enough for its outer peripheral portion to reach the ciliary groove, while the openings 25 need to be formed at positions to be sutured with the periphery of the ciliary body.

When the internal apparatus 20 is placed inside the eye, the iris may undergo abrasion with the substrate 23 and become inflamed, etc. In order to avoid such inconvenience, part of the iris that comes in contact with the substrate 23 may be removed. Removal of the iris causes the outward appearance of the patient's eye to deteriorate. However, in the embodiment, because the iris pattern 22c is provided to one surface of the magnetic core 22a as shown in FIG. 3B, a portion artificially imitating the iris is left behind the iris even when the iris is removed, and deterioration of the outward appearance of the patient's eye is reduced to the least possible degree.

Further, the power acquiring portion 22 is placed behind the iris in the embodiment. The invention, however, is not limited to this arrangement, and for example, the power acquiring portion 22 may be placed by positioning the anterior ocular segment on the surface side of the iris (a space between the cornea and the iris) or the lens capsule to the pupil and the opening in the magnetic core 22a.

As has been described, the coil 22b is wound around the magnetic core 22a in the embodiment, which improves power transmission efficiency in comparison with the case of using a coil having an air core. Further, because a hollow magnetic core provided with an opening in the central portion is used as the magnetic core 22a, the magnetic core 22a is lighter in weight than a magnetic core having no opening, and can be therefore readily placed inside the eye. Further, by positioning the opening in the magnetic core 22a at the pupil, it is possible to introduce light from outside the eye to the inside of the eye through the opening.

Meanwhile, as to the external apparatus 10, the user puts on the visor 11 and positions the power supply portion 13 in front of his eyes. When a current flows from the power apparatus 12 to the power supply portion 13, electromagnetic induction is induced between the primary coil 13b and the secondary coil 22b, whereby power is supplied to the internal apparatus 20.

Light from outside the eye passes through the opening in the magnetic core 13a and reaches inside the eye. The thus-reached light then passes through the opening in the magnetic core 22a, and is received on the light-receiving surface of the light-receiving elements 32 through the optical member 24. Signals from the light-receiving elements 32 are transmitted to the control circuit 34. The control circuit 34 converts the thus-received signals into an electrical signal of a pulse shape needed to obtain vision, and applies a predetermined voltage between the tacks 35 and the corresponding stimulating electrodes 33. When a voltage is applied between the tacks 35 and the corresponding stimulating electrodes 33, a current of a specific pulse shape passes through the retina from the stimulating electrodes 33 and r aches the tip ends of the tacks 35. Cells forming the retina, such as bipolar cells and retinal gangilion cells, are thereby electrically stimulated, and vision can be thus regenerated or restored.

While the embodiment above described the artificial vision system of the internal imaging type, it should be appreciated that the invention is applicable to an artificial vision system of the external imaging type. In this case, the external apparatus 10 is provided with an imaging unit, such as a CCD camera, an information processing unit for obtaining stimulating pulse data (control signal) used for regeneration or restoration of vision by applying predetermined processing on image information obtained from the imaging unit, and a transmitting unit for transmitting the stimulating pulse data to the internal apparatus 20. Meanwhile, the internal apparatus 20 is provided with a receiving unit for receiving the stimulating pulse data, instead of the optical member 24 placed in the magnetic core 22a. Alternatively, the power supply portion 13 and the power acquiring portion 22 may serve as the transmitting unit and the receiving unit, respectively.

Figure 6:
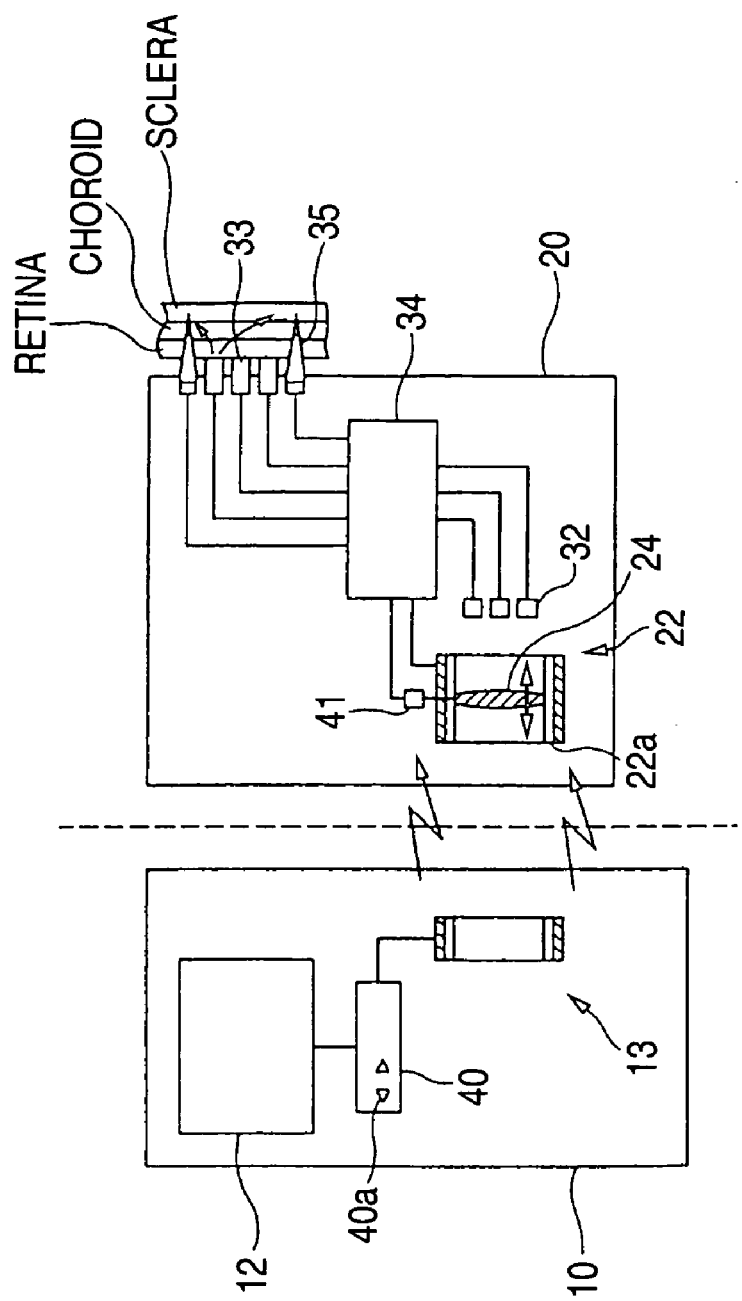
FIG. 6 is a schematic block diagram of a control system in an artificial vision system additionally provided with an adjusting mechanism.

While the optical member 24 is provided in the magnetic core 22a in the embodiment, an adjusting mechanism may be additionally provided by allowing the optical member 24 to move in the axial direction of the magnetic core 22a. FIG. 6 is a schematic block diagram showing an example when the adjusting mechanism is added. Components having similar functions as those shown in FIG. 5 are labeled with the same reference numerals, and an explanation of such components is omitted for ease of explanation.

Numeral 40 denotes a control portion provided in the external apparatus 10. The control portion 40 is provided with a switch 40a. With the use of the switch 40a, the optical member 24 is moved to focus on a given object point at a predetermined distance position. Further, the control portion 40 converts a power signal from the power apparatus 12 and a signal from the switch 40a into a digital signal, so that power information and driving information of the optical member 24 can be transmitted to the internal apparatus 20 by means of the power supply portion 13.

The optical member 24 is attached movably in the axial direction of the magnetic core 22a, and is moved back and forth in the axial direction by a compact motor 41. When the user manipulates the switch 40a of the controller 40, a signal is transmitted from the power supply portion 13 to the internal apparatus 20 in the form of a digital signal. The power information and the driving information of the optical member 24 are transmitted in a time divisional manner, and the thus-transmitted power information and driving information of the optical member 24 are received alternately in the power acquiring portion 22 to be further transmitted to the control circuit 34. The control circuit 34 uses the thus-received power information as power to drive the internal apparatus 20. Further, the control circuit 34 drives the compact motor 41 based on the thus-received driving information of the optical member 24, and thereby moves the optical member 24. The user is thus able to bring the focus on a given object point at an arbitrary position freely. By using the arrangement described above, it is possible to provide the internal apparatus 20 with focusing, telescopic, and wide-angle functions. Moreover, a quantity of light or the like can be adjusted by placing an opening-varying mechanism in front or behind the magnetic core 22a or in the opening thereof.

Further, such an adjusting mechanism may be provided to the external apparatus 10. In this case, the external apparatus 10 is provided with an optical system enabling focusing, telescopic, and wide-angle functions.

The opening in the magnetic core is situated at the pupil in the embodiment. The invention, however, is not limited to this arrangement, and the magnetic core may be situated at a position other than the pupil as long as incoming outside light is not blocked. In this case, light from outside the eye cannot pass through the opening in the magnetic core; however, there are merits in that power supply efficiency can be increased by winding a coil around the magnetic core, and in that the weight can be reduced by using a hollow magnetic core.

As has been described, according to the invention, the artificial vision system can supply power efficiently to an apparatus to be placed inside the eye while being used suitably as an intraocular apparatus.

What is claimed is:

1. An artificial vision system for regenerating or restoring vision of an eye of a patient comprising:
    a power acquiring unit which is disposable inside the eye, in the vicinity of the iris, which unit includes a ring-shaped magnetic core having an opening and a coil wound around a periphery of the magnetic core, and is adapted to acquire power from outside a body using electromagnetic induction; and
    a plurality of electrodes which is adapted to be provided at the retina and is adapted to electrically stimulate cells constituting the retina using power obtained by the power acquiring unit.

2. The artificial vision system according to claim 1, wherein the power acquiring unit is disposed so that the opening of the magnetic core is located at a pupil.

3. The artificial vision system according to claim 2, wherein the opening of the magnetic core is made as large as or larger than a maximum size of the pupil.

4. The artificial vision system according to claim 2 further comprising a plurality of light-receiving elements which are provided so as to correspond to the plurality of electrodes and disposable inside the eye so as to receive light from outside the body through the opening of the magnetic core.

5. The artificial vision system according to claim 4 further comprising an optical member which is disposed on an axis of the magnetic core and is adapted to form an image of an object point at a predetermined distance position in front of the eye on a light-receiving surface of the plurality of light-receiving elements.

6. The artificial vision system according to claim 5, wherein the optical member is placed in the opening of the magnetic core.

7. The artificial vision system according to claim 5 further comprising a moving unit which is adapted to move the optical member in an axial direction of the magnetic core.

8. The artificial vision system according to claim 2, wherein an iris pattern is provided to one of the magnetic core, a substrate on which the magnetic core is disposed and a coating surface embedding the magnetic core.

9. The artificial vision system according to claim 2 further comprising a power supply unit which is disposable in front of the eye, includes a magnetic core having an opening and a coil wound around the magnetic core, and is adapted to supply the power to the power acquiring unit using the electromagnetic induction.

10. An artificial vision system for regenerating or restoring vision of an eye of a patient comprising:
    a power acquiring unit which is disposable inside the eye, which unit includes a magnetic core having an opening and a coil wound around the magnetic core, and is adapted to acquire power from outside a body using electromagnetic induction;
    a plurality of electrodes which is adapted to be provided at the retina and is adapted to electrically stimulate cells constituting the retina;
    a plurality of light-receiving elements which are provided so as to correspond to the plurality of electrodes and disposable inside the eye so as to receive light from outside the body through the opening of the magnetic core; and
    an optical member which is disposed on an axis of the magnetic core and is adapted to form an image of an object point at a predetermined distance position in front of the eye on a light-receiving surface of the plurality of light-receiving elements; and
    wherein the power acquiring unit is disposed so that the opening of the magnetic core is located at a pupil.

11. The artificial vision system according to claim 10, wherein the optical member is placed in the opening of the magnetic core.

12. The artificial vision system according to claim 10, further comprising a moving unit which is adapted to move the optical member in an axial direction of the magnetic core.

* * * * *